| United States Patent [19] | [11] Patent Number: 4,587,344 |
| Ryan | [45] Date of Patent: May 6, 1986 |

[54] ISOTHIOUREA SYNTHESIS PROCESS

[75] Inventor: Charles W. Ryan, Indianapolis, Ind.

[73] Assignee: Eli Lilly and Company, Indianapolis, Ind.

[21] Appl. No.: 676,370

[22] Filed: Nov. 29, 1984

Related U.S. Application Data

[63] Continuation of Ser. No. 464,296, Feb. 7, 1983, abandoned.

[51] Int. Cl.[4] .......................................... C07D 277/30
[52] U.S. Cl. .................................................. 548/205
[58] Field of Search ........................ 548/202, 203, 205

[56] References Cited

U.S. PATENT DOCUMENTS 4,285,952  8/1981  Durant ............................... 424/263
4,375,547  3/1983  Pioch ................................. 548/205

FOREIGN PATENT DOCUMENTS 2084581  4/1982  United Kingdom ................ 548/202

*Primary Examiner*—Robert Gerstl
*Attorney, Agent, or Firm*—Bruce J. Barclay; Arthur R. Whale

[57] ABSTRACT

N-methyl-S-methyl-N'-[2-(2-dimethylaminomethyl-thiazol-4-ylmethylthio)ethyl]isothiourea is prepared by the reaction of 2-dimethylaminomethyl-4-(2-aminoethyl)thiomethylthiazole with methylcarbonimidodithioic acid, dimethyl ester, and is a useful intermediate for the preparation of nizatidine, a pharmaceutically valuable H$_2$-receptor inhibitor.

2 Claims, No Drawings

ISOTHIOUREA SYNTHESIS PROCESS

This application is a continuation of application Ser. No. 464,296, filed Feb. 7, 1983 now abandoned.

BACKGROUND OF THE INVENTION

1. Field of the Invention

The present invention belongs to the field of pharmaceutical chemistry, and provides a useful intermediate for the synthesis of nizatidine, an important and relatively new H$_2$-receptor antagonist, which is used primarily for the treatment of gastric ulcers.

2. State of the Art

The H$_2$ receptor antagonists have been studied for some years, and a very extensive literature has been built up around them. The most prominent individual drugs are probably cimetidine, N-cyano-N'-methyl-N''-[2-([(5-methyl-1H-imidazol-4-yl)methyl]thio)ethyl]-guanidine, and ranitidine, N-methyl-N'-2-(5-dimethylaminomethylfur-2-ylmethylthio)ethyl-2-nitro-1,1-ethenediamine. Cimetidine is taught by Durant et al., U.S. Pat. No. 3,950,333, and ranitidine is disclosed by Price et al., in U.S. Pat. No. 4,128,658.

Further disclosures from the voluminous H$_2$-receptor literature which are particularly pertinent to the present invention include U.S. Pat. No. 4,239,769, of Price et al., which discloses at columns 3 and 4 a synthesis process which proceeds through an S-methyl isothiourea intermediate. The objective of that synthesis, however, is a class of compounds wherein the heterocyclic ring is thiophene.

U.S. Pat. No. 3,950,333 also makes use of a number of S-methyl isothiourea intermediates, such as those of Examples 55, 64, 75, 121 and others.

British Pat. No. 2,067,987, of Crenshaw et al., shows as its Example 22E the compound which is the starting compound for the present invention, 4-(2-aminoethyl)-thiomethyl-2-dimethylaminomethylthiazole.

U.S. Pat. No. 4,200,578, of Algieri et al., shows 2-nitro-1,1-ethenediamine compounds, having a relationship to the ultimate product of the present invention, but wherein the terminal nitrogen is substituted with an alkynyl group. Algieri's compounds have a thiazole ring, but the patent states a preference for attaching the "tail" ending in the ethenediamine group to the 2-position of the thiazole ring, rather than the 4-position.

Nizatidine, the ultimate product of the present invention, is disclosed in allowed U.S. application Ser. No. 319,155, of Pioch.

SUMMARY OF THE INVENTION

The present invention provides the isothiourea of the formula

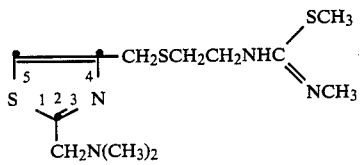

The invention also provides the process for preparing the above compound which comprises reacting the methylthioethylamine of the formula

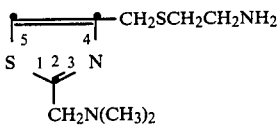

with methylcarbonimidodithioic acid, dimethyl ester, of the formula

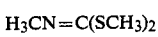

$$H_3CN=C(SCH_3)_2$$

in the presence of at least about one mole of an acid per mole of the thiazole.

DESCRIPTION OF THE PREFERRED EMBODIMENTS

In this document, all temperatures are described in degrees Celsius.

The intermediate of this invention is used to prepare nizatidine by reacting it with nitromethane. The reaction is preferably carried out in a secondary alkanol such as 2-butanol or isopropanol. Other solvents which can be used but provide lesser yields include nitriles such as acetonitrile and propionitrile, esters such as ethyl acetate, butyl acetate and the like, and primary alkanols such as ethanol and isobutanol.

It is possible to carry out the reaction with nitromethane without any additional solvent, but it is preferable to use some solvent. It has been found most advantageous to use about equal weights of solvent and nitromethane, and to use a substantial excess of nitromethane, such as at least about 5 moles per mole of the isothiourea. Extremely large excesses in the range of from about 10 to about 25 moles of nitromethane, or even more, may be used if desired and will cause no difficulty.

It is desirable to carry out the nitromethane reaction at an elevated temperature, in the range of about 50–150°, and about 100° has been found to be especially convenient. The reaction is not particularly rapid, even at elevated temperature, and several hours reaction time is necessary. Periods of about 12–24 hours are convenient. It will be understood that higher temperatures will usually allow the process to proceed at a higher rate, and that the process may be carried out under pressure, if desired, to enable higher temperatures to be used.

As is usually the case in organic chemistry, the most advantageous operating conditions, and especially reaction time, are chosen by a compromise between throughput, usually maximized by short reaction times and high temperatures, and yield, which is usually maximized by long reaction times and moderate temperatures. The most advantageous compromise is routinely determined by process chemists in individual situations.

Preparation 1 below illustrates a preferred synthesis of nizatidine.

The starting compounds used in the process of this invention to prepare the product of this invention are known compounds. The thiazole is disclosed in British Pat. No. 2,067,987, and the dithioic acid ester is disclosed by Ainley et al., *J. Chem. Soc.* 147–52 (1944). It is not necessary to purify the starting compounds.

The process of this invention is preferably carried out in water, an alkanol such as ethanol or isopropanol, or an aqueous alkanol. Higher molecular weight alcohols such as 2-butanol can be used but give less yield and a less pure product. Solvents other than alkanols, such as esters, halogenated alkanes, ethers, and aromatics can be used if necessary but are by no means preferred.

The reaction is carried out in the presence of at least about 1 mole of an acid. Both mineral acids and organic acids are useful, and the acid may be added as such or as an acid addition salt of either reactant. The examples below show various acids in use, including very strong acids such as hydrochloric acid and methanesulfonic acid, as well as relatively weak acids such as oxalic acid. Any practical organic or inorganic acid may be used as is convenient in the circumstances, such as acetic acid, butyric acid, benzoic acid, hydrobromic acid, phosphoric acid, nitric acid, sulfuric acid, maleic acid and the like.

When an aqueous or aqueous alkanolic reaction medium is used, it is highly preferred to adjust its pH to about 5–7. Both product purity and yield are improved by doing so. Depending on the nature of the acid used in the mixture, it may be necessary to add some base to obtain the desired pH. The identity of the base is not important, so long as the solubilities of the substances are taken into account.

Bases such as potassium, lithium and sodium hydroxides, carbonates and bicarbonates, tertiary amines including pyridine, triethylamine and triethanolamine, and the like may be used as is convenient in the circumstances. The acid/base balance is less important when a nonaqueous reaction mixture is used.

Operation in water as the reaction solvent is preferred. The examples below show the use of both aqueous reaction mixtures and mixtures based on alcohols, as well as the use of both dilute aqueous acid and relatively concentrated acids.

The reaction of this invention takes place at moderately elevated temperatures in reasonable periods of time. Temperatures in the range of from about 50° to about 125° are convenient. It is particularly convenient, as usual in organic chemistry, to operate at the ambient pressure reflux temperature of the reaction mixture, but there is no objection to operating under pressure in order to raise the boiling point of the mixture. Particularly advantageous temperatures are in the range of about 75–100°. Reaction times in the range of from a few hours to 1 day are appropriate; the examples below show excellent yields of product obtained in times in the range of about 3–8 hours.

A chemist would expect that the starting compounds used in the present process would smell quite unpleasant, and such is indeed the case. The intermediates should be handled and the process should be carried out in equipment which is substantially vaportight to avoid contaminating the process area with evil-smelling vapors, and the process wastes must be disposed of in a suitable manner.

The product of the process is conveniently isolated in good purity by conventional means as shown by the examples below. For example, the mixture may be neutralized and extracted with an organic solvent, and the product isolated from the aqueous layer by making it highly basic and extracting with a suitable organic solvent, especially dichloromethane.

The following preparation illustrates the use of the product of this invention as the intermediate for the synthesis of nizatidine.

PREPARATION 1

N-methyl-N'-[2-(2-dimethylaminomethylthiazol-4-ylmethylthio)ethyl]-2-nitro-1,1-ethenediamine Nine g. of N-methyl-S-methyl-N'-[2-(2-dimethylaminomethylthiazol-4-ylmethylthio)ethyl]isothiourea was stirred in 45 ml. of nitromethane and 45 ml. of 2-butanol in a 95° bath for 20 hours. The reaction mixture was then evaporated to dryness on a warm water bath under vacuum, and the residue was dissolved in 50 ml. of ethyl acetate and stirred at ambient temperature. A solid crystallized out, and the solution was cooled in an ice bath for 30 minutes. The mixture was then filtered and the solids were washed with cold ethyl acetate and dried in air to obtain 6.5 g. of the desired product in crude form, which was found to be 88.6% pure, with 6 impurities, by high performance liquid chromatography analysis (HPLC). Six g. of the crude product was dissolved in 50 ml. of warm denatured ethanol, and the solution was stirred while it cooled to ambient temperature. The crystals were collected by filtration, washed with denatured ethanol and air dried overnight to obtain 4.61 g. of purified nizatidine, m.p. 134–136°, found to be 96.7% pure by HPLC.

The process of this invention is further described by the following examples.

EXAMPLE 1

N-methyl-S-methyl-N'-[2-(2-dimethylaminomethylthiazol-4-ylmethylthio)ethyl]isothiourea Two g. of 2-dimethylaminomethyl-4-(2-aminoethyl)-thiomethylthiazole, 25 ml. of denatured ethanol, 0.72 ml. of concentrated hydrochloric acid and 1.16 g. of methylcarbonimidodithioic acid, dimethyl ester, were added to a flask and heated under reflux for 16 hours. The reaction mixture was then evaporated to an oily residue under vacuum, and the residue was taken up in 25 ml. of water and extracted with two 15 ml. portions of diethyl ether. The aqueous layer was cooled and 3 ml. of 50% aqueous sodium hydroxide was added. The aqueous solution was then extracted with two 20 ml. portions of diethyl ether, and the extract was evaporated to dryness under vacuum to obtain 2.0 g. of crude product, which was identified by its mass spectrum, showing a molecular ion of weight 318, and by its nuclear magnetic resonance spectrum; $^1$H NMR (CDCl$_3$) δ7.07 (s, 1H), 3.87 (s, 2H), 3.75 (s, 2H), 3.42 (t, 2H), 2.75 (m, 2H) and 2.33 (s, 9H).

EXAMPLE 2

N-methyl-S-methyl-N'-[2-(2-dimethylaminomethylthiazol-4-ylmethylthio)ethyl]isothiourea One g. of the oxalate salt of 2-dimethylaminomethyl-4-(2-aminoethyl)thiomethylthiazole was dissolved in 10 ml. of denatured ethanol and 4.8 ml. of 1N sodium hydroxide solution. To the mixture was added 0.36 g. of methylcarbonimidodithioic acid, dimethyl ester, and the reaction mixture was stirred under reflux for 16 hours. The mixture was then evaporated under vacuum, and the residue was taken up in 12 ml. of water and 1.5 ml. of 50% aqueous sodium hydroxide. The solution was extracted twice with 25 ml. portions of diethyl ether, and the organic layers were combined, dried over potassium carbonate and evaporated under vacuum to obtain 0.65 g. of the desired product in crude form. It was identified by nuclear magnetic resonance analysis as being identical to the product of Example 1.

EXAMPLE 3

N-methyl-S-methyl-N'-[2-(2-dimethylaminomethyl-thiazol-4-ylmethylthio)ethyl]isothiourea To a flask fitted with a condenser, stirrer and thermometer were added 20 g. of the dioxalate salt of 2-dimethylaminomethyl-4-(2-aminoethyl)thiomethyl-thiazole, and 50 ml. of water. The pH of the solution was adjusted to 6.1 by the addition of 52 ml. of 2N aqueous potassium hydroxide, and 7.5 g. of methylcarbonimidodithioic acid, dimethyl ester, was added. The mixture was stirred at 75° for 3 hours, and was then cooled to ambient temperature. Its pH was adjusted to 6.5 by addition of 3.2 ml. of 2N aqueous potassium hydroxide, and 100 ml. of dichloromethane was added with vigorous mixing. The pH was adjusted to 6.5 again with 1 ml. of 2N aqueous potassium hydroxide, and the organic layer was separated and discarded. The aqueous layer was mixed with 100 ml. of additional dichloromethane, and its pH was adjusted to 13 by addition of 55 ml. of 2N aqueous potassium hydroxide. The organic layer was separated, dried over potassium carbonate and evaporated under vacuum to obtain 13.1 g. of product, which was found by NMR analysis to be substantially identical to that of Example 1. Its purity was 94.6% by high performance liquid chromatographic analysis.

EXAMPLE 4

N-methyl-S-methyl-N'-[2-(2-dimethylaminomethyl-thiazol-4-ylmethylthio)ethyl]isothiourea Ten g. of 2-dimethylaminomethyl-4-(2-aminoethyl)-thiomethylthiazole was dissolved in 100 ml. of isopropanol, and 2.8 ml. of methanesulfonic acid was added, followed by 6.5 g. of methylcarbonimidodithioic acid, dimethyl ester. The mixture was stirred under reflux for 16 hours, and was evaporated under vacuum to obtain a residue, which was taken up in 100 ml. of water. The solution was extracted with two 25 ml. portions of dichloromethane, and the aqueous layer was cooled. Fifty ml. of dichloromethane and 15 ml. of 50% aqueous sodium hydroxide were added. The layers were separated, and the solution was extracted again with 50 ml. of dichloromethane. The organic layers were combined, dried over potassium carbonate and evaporated under vacuum to obtain 10.3 g. of product, substantially identical to that of Example 1, which was 96.7% pure by HPLC analysis.

EXAMPLE 5

N-methyl-S-methyl-N'-[2-(2-dimethylaminomethyl-thiazol-4-ylmethylthio)ethyl]isothiourea Two g. of 2-dimethylaminomethyl-4-(2-aminoethyl)-thiomethylthiazole and 1.49 g. of methylcarbonimidodithioic acid, dimethyl ester, hydrochloride, were stirred in 20 ml. of isopropanol under reflux for 16 hours. The mixture was then evaporated under vacuum, and the residue was dissolved in 20 ml. of water, extracted with dichloromethane and worked up as described in Example 4 to obtain 2.5 g. of product, which was found to be 95.7% pure by HPLC analysis. The product was identified by NMR analysis as substantially identical to the product of Example 1.

EXAMPLE 6

N-methyl-S-methyl-N'-[2-(2-dimethylaminomethyl-thiazol-4-ylmethylthio)ethyl]isothiourea A solution of 1.1 g. of 2-dimethylaminomethyl-4-(2-aminoethyl)thiomethylthiazole in 9 ml. of water was made acid to pH 5.9 with 0.65 g. of oxalic acid dihydrate, and 0.7 g. of methylcarbonimidodithioic acid, dimethyl ester, was added. The mixture was stirred at 75° overnight, and was then cooled. Its pH was adjusted to 6.5 by addition of 2N aqueous potassium hydroxide, and it was extracted with 12 ml. of dichloromethane. The aqueous layer was worked up as described in Example 4 to obtain 1.4 g. of product, which was 95.2% pure by HPLC analysis and was found to be substantially identical to the product of Example 1 by NMR analysis.

EXAMPLE 7

N-methyl-S-methyl-N'-[2-(2-dimethylaminomethyl-thiazol-4-ylmethylthio)ethyl]isothiourea The process of Example 6 was repeated, except that the initial acidification was carried out by the addition of 0.6 ml. of glacial acetic acid. The product was 1.3 g. of the desired product, 93.1% pure by HPLC analysis, and substantially identical to the product of Example 1 by NMR analysis.

EXAMPLE 8

N-methyl-S-methyl-N'-[2-(2-dimethylaminomethyl-thiazol-4-ylmethylthio)ethyl]isothiourea To a flask were added 10 g. of 2-dimethylaminomethyl-4-(2-aminoethyl)thiomethylthiazole, 14.5 ml. of water, 73.5 ml. of 1N hydrochloric acid and 6.4 g. of methylcarbonimidodithioic acid, dimethyl ester. The mixture was stirred at 75° under a condenser for 6 hours, and was then cooled to ambient temperature. The mixture was worked up as described in Example 4 above to obtain 11.3 g. of product, which was 93.7% pure by HPLC analysis, and which was substantially identical to the product of Example 1 by NMR analysis.

I claim:

1. A process for preparing N-methyl-S-methyl-N'-[2-(2-dimethylaminomethylthiazol-4-ylmethylthio)ethyl]isothiourea which process comprises reacting 2-dimethylaminomethyl-4-(2-aminoethyl)thiomethylthiazole with methylcarbonimidodithioic acid, dimethyl ester in the presence of at least about 1 mole of an acid per mole of the thiazole.

2. A process of claim 1 wherein the reaction is carried out in an aqueous or aqueous alkanolic reaction mixture, and the pH is about 5-7.

* * * * *